United States Patent

Kanda et al.

Patent Number: 5,851,732
Date of Patent: Dec. 22, 1998

[54] PLASMA DISPLAY PANEL DEVICE FABRICATION UTILIZING BLACK ELECTRODE BETWEEN SUBSTRATE AND CONDUCTOR ELECTRODE

[75] Inventors: Hiroshi Kanda, Yakohama, Japan; Jerome David Smith, Cary; Terry R. Suess, Raleigh, both of N.C.

[73] Assignee: E. I. du Pont de Nemours and Company, Wilmington, Del.

[21] Appl. No.: 812,230

[22] Filed: Mar. 6, 1997

[51] Int. Cl.⁶ ..................................................... G03C 5/00
[52] U.S. Cl. ............................................. 430/321; 430/312
[58] Field of Search ........................................ 430/321, 312

[56] References Cited

U.S. PATENT DOCUMENTS

| | | | |
|---|---|---|---|
| 5,032,490 | 7/1991 | Nebe et al. | 430/270.1 |
| 5,035,980 | 7/1991 | Nebe et al. | 430/281.1 |
| 5,049,480 | 9/1991 | Nebe et al. | 430/270.1 |
| 5,260,163 | 11/1993 | Nebe et al. | 430/325 |

FOREIGN PATENT DOCUMENTS

4-272634  9/1992  Japan .

Primary Examiner—M. Nuzzolillo
Assistant Examiner—Laura Weiner

[57] ABSTRACT

The present invention is directed to a PDP device fabricated by using photosensitive thick film conductor compositions wherein a black electrode is present between the substrate and a conductor arrangement electrode. Also, the invention is directed to methods for fabricating the PDP device.

12 Claims, 5 Drawing Sheets

PLASMA DISPLAY PANEL DEVICE FABRICATION UTILIZING BLACK ELECTRODE BETWEEN SUBSTRATE AND CONDUCTOR ELECTRODE

FIELD OF THE INVENTION

The present invention is directed to a plasma display panel device and a method of fabricating the same and in particular, to an alternating-current plasma display panel (AC PDP) device and a method of fabricating the AC PDP.

BACKGROUND OF THE INVENTION

Figure 4:
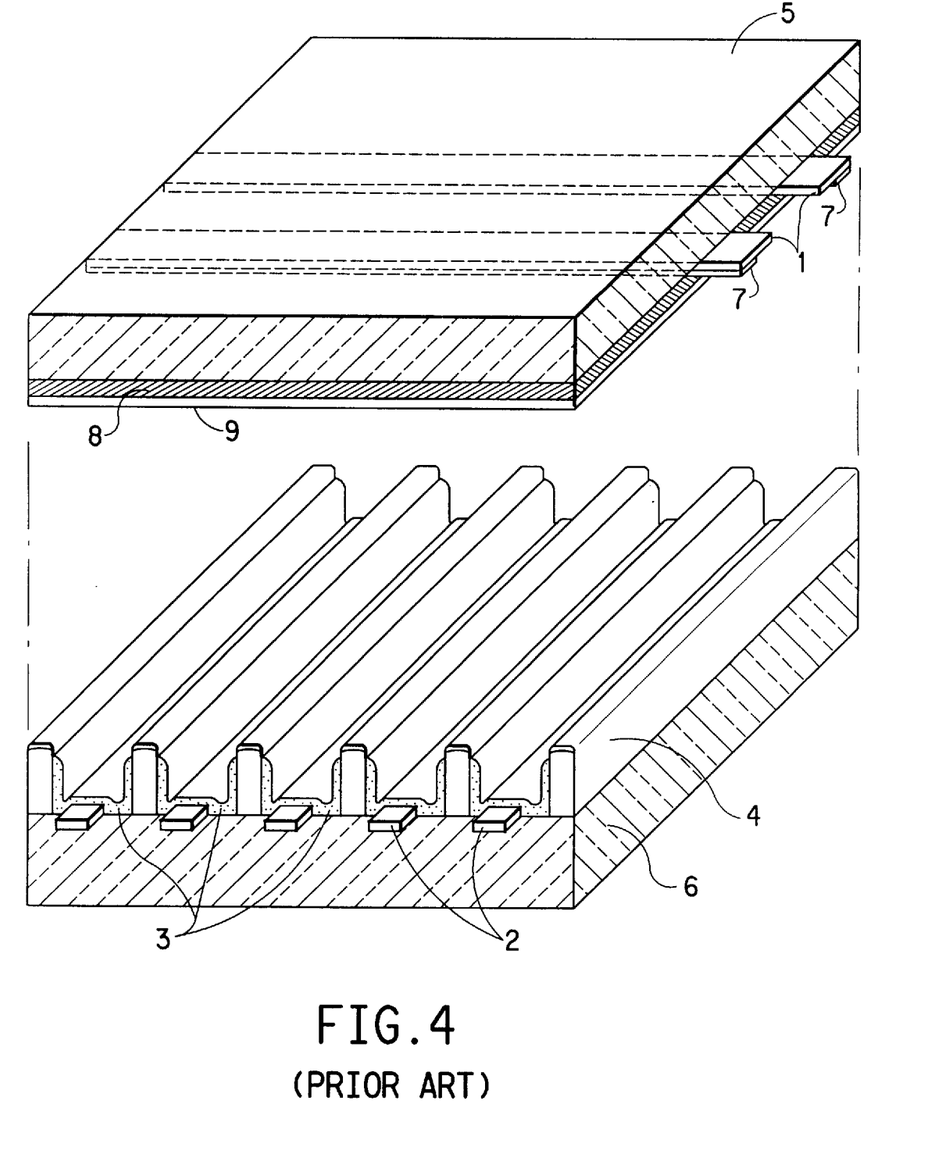
FIG. 4 is an illustration of a prior art AC PDP device.

The plasma display panel (PDP) typically comprises a pair of forward and backward insulation substrates arranged in opposition to each other to form a plurality of cells as display elements each defined by the insulation substrates supported with a constant interval and cell barriers arranged between the insulation substrates, two crossing electrodes disposed on internal surfaces of the insulation substrates with a dielectric layer interposed between the electrodes which cause electric discharge in a plurality of cells by application of A.C. voltage therebetween resulting into making phosphor screens formed on a wall surface of the cell barrier, emit light and displaying images by a light passed through the transparent insulation substrate. More particularly, as shown in FIG. 4 transparent electrodes 1 and addressing electrodes 2 are arranged in the form of a matrix and plasma discharge is produced at selected intersecting points of such electrodes 1 and 2 producing the fluorescent material 3 which emits light. Cell barriers 4 being of matrix or linear structure as a display element is arranged between the front glass substrate 5 and the rear glass substrate 6 to form a plurality of cells. Bus electrodes 7 are used for connecting transparent electrodes 1 for display lines which are sequentially selected one by one, erasing cells of the selected display line, and displaying data to the selected cells are shown to be formed on the surface of the transparent electrodes 1 on the front glass substrate 5, a dielectric layer 8 serves as an insulation layer and is formed over the transparent electrodes 1 and bus electrodes 7. A protective MgO film 9 is formed over the dielectric layer 8.

Resolution and brightness of the images in the AC PDP device depend on electrode width, interconnecting conductor pitch and transparency of the dielectric layer. It is difficult to obtain fine line and space resolution for the formation of the electrodes and interconnecting conductor patterns when these materials are applied by conventional patterning techniques such as screen printing, sputtering or chemical etching methods. Moreover, to improve the display contrast, it is essential to decrease the reflection of external light from the electrodes and conductors arranged on the front glass substrate. This reflection decrease can be most easily accomplished by making the electrodes and conductors black as viewed through the front plate of the display. The present invention is directed to such an accomplishment.

SUMMARY OF THE INVENTION

The present invention is directed to a PDP device fabricated by using photosensitive thick film conductor compositions wherein a black electrode is present between the substrate and a conductor arrangement electrode. Also, the invention is directed to methods for fabricating the PDP device.

More particularly, the present invention is directed to an AC PDP device comprising front and rear insulating substrates spaced apart from each other; an electrode arrangement comprising a first group of electrode composites in parallel facing a discharge space filled with ionizable gas, and a second group of electrode composites; the first and second group of electrode composites being positioned face to face in an orthogonal relationship across the discharge space, formed on the surface of the insulating substrates with specified electrode patterns, the electrode arrangement being coated with a dielectric on at least one of the insulating substrates, wherein the electrode composite on at least the front insulating substrate comprises;

a conductor electrode arrangement comprising a group of conductor electrodes formed on each substrate being connected to the respective bus conductors on the same substrate and;

a photoformable black electrode comprising a conductive layer of at least one of $RuO_2$, ruthenium based polynary oxide or mixtures thereof formed between the substrate and conductor electrode arrangement.

The invention is further directed to a method for fabricating a AC PDP device comprising the sequential steps:

(1) applying a photosensitive black composition on a substrate, wherein the black conductive composition comprises an admixture of (a) conductive particles of at least one of $RuO_2$, ruthenium based polynary oxide or mixtures thereof, (b) at least one inorganic binder, (c) organic, carboxylic acid containing polymeric binder, (d) photoinitiation system, and (e) photohardenable monomer;

(2) imagewise exposing the black composition to actinic radiation to define the specified pattern;

(3) developing the exposed black composition in a basic aqueous solution to remove the composition in areas not exposed to actinic radiation;

(4) firing the developed black composition, forming a black conductive component on the substrate;

(5) applying a photosensitive conductive composition which forms a conductor electrode and comprises an admixture of (a) conductive particles of at least one metal selected from a group of Au, Ag, Pd, Pt and Cu, or combinations thereof, (b) at least one inorganic binder, (c) organic, carboxylic acid containing polymeric binder, (d) photoinitiation system, and (e) photohardenable monomer;

(6) imagewise exposing the conductive composition to actinic radiation to define the electrode pattern;

(7) developing the exposed photosensitive conductive composition in a basic aqueous solution to remove the composition in areas not exposed to actinic radiation;

(8) firing the developed conductive composition forming the conductor electrodes on top of the arrangement of black electrodes on the substrate.

In addition the invention is directed to a method for simultaneously developing the black electrode composition and the conductor electrode composition.

The invention is still further directed to a method for simultaneously exposing and developing of the black electrode composition and the conductor electrode composition.

DETAILED DESCRIPTION OF THE INVENTION

Figure 1:
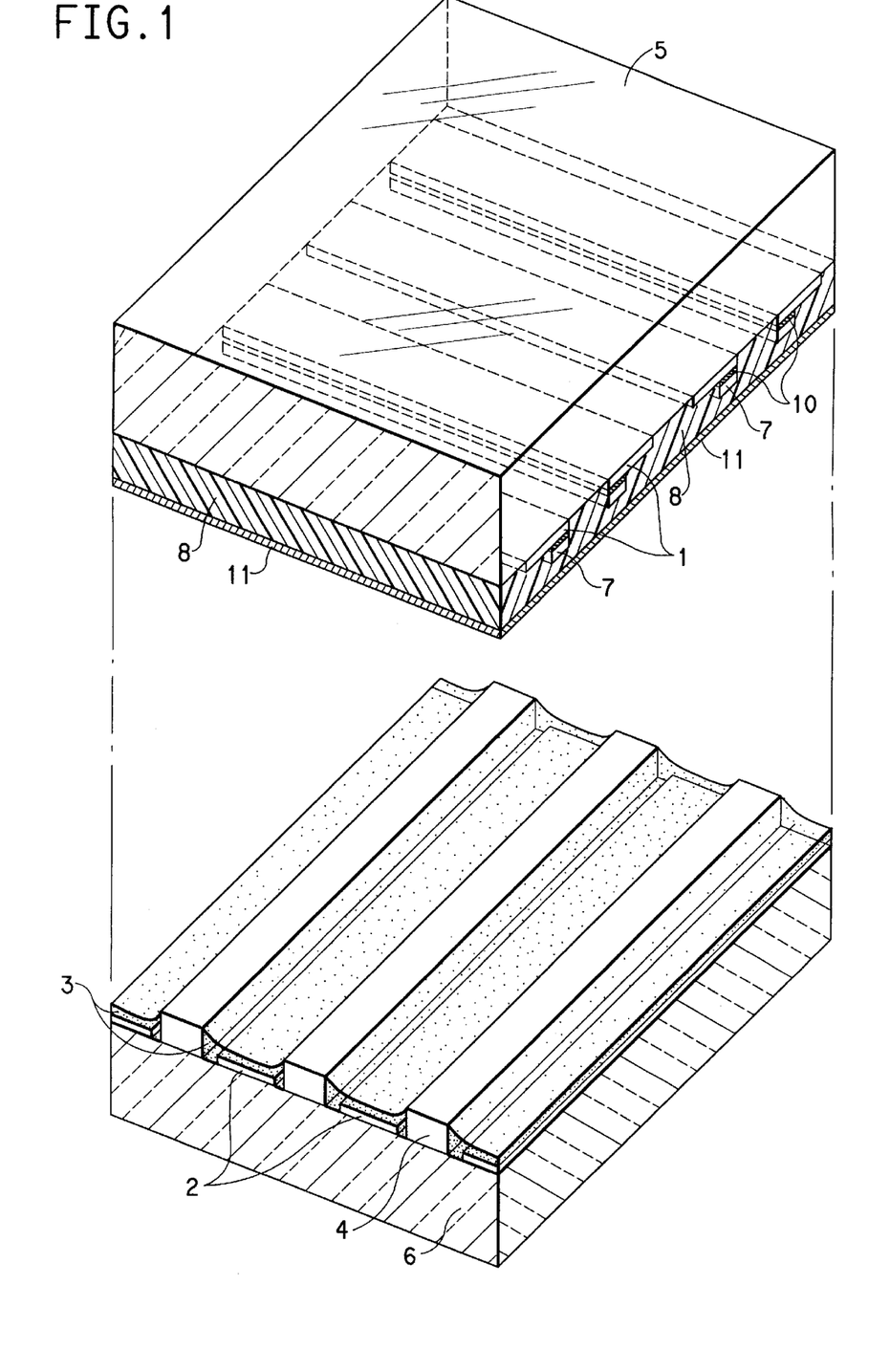
FIG. 1 is an illustration of a AC PDP device fabricated in accordance with the present invention.

FIG. 1 is an illustration of a AC PDP fabricated in accordance with the present invention. Therefore, as illustrated in FIG. 1, the present invention describes an AC plasma display panel device, characterized as having a configuration wherein the improvement comprises an underlying transparent electrode 1 formed on a glass substrate, a black electrode 10 formed on the underlying transparent electrode 1 wherein in black electrode uses a photosensitive conductor composition which may be applied as a paste or dry film comprising at least one $RuO_2$, ruthenium based polynary oxides or mixtures thereof and a top layer which is a bus conductor electrode 7, formed on the underlying black electrode 10, wherein the bus conductor electrode using a photosensitive conductor composition containing conductive particles being selected from a group of Au, Ag, Pd, Pt and Cu metals, or combinations thereof. The black electrode 10 and bus conductor electrode 7 are patterned by imagewise exposure to actinic radiation, developed in a basic aqueous solution and fired at an elevated temperature to remove the organic components and to sinter the inorganic materials. The black electrode 10 and bus conductor electrode 7 are patterned using the same, or very similar images. The final result is a fired electrode composite that appears black on the transparent electrode 1 surface, decreasing the reflection of external light from the electrode composites arranged on the front glass substrate, and has good conductivity. As used herein, the term "black" refers to color wherein the black color exhibits a visual significant contrast versus a white background. Therefore, the term is not necessarily limited to black which possesses the absence of color. To the contrary, although shown in FIG. 1, the underlying transparent electrode is not necessary to the practice of the plasma display device of the present invention.

If present, the transparent electrodes 1 are formed using $SnO_2$ or ITO by ion spattering or plating, chemical vapor deposition or electric deposition techniques. In the present invention, such transparent electrode configurations and the formation processes are well known in the art of the conventional AC PDP technology.

Again, referring to FIG. 1, the AC plasma display panels device are based on glass substrates having patterned and fired metallizations coated by a dielectric overglaze 8 which is then coated MgO 11.

The conductor lines are uniform in line width and are not pitted or broken, have high conductivity, optical clarity and transparency between lines.

A process for making both the bus and the black electrodes over the optional transparent electrode on the glass substrate of a front plate of the PDP device are discussed herein below.

Figure 2A:
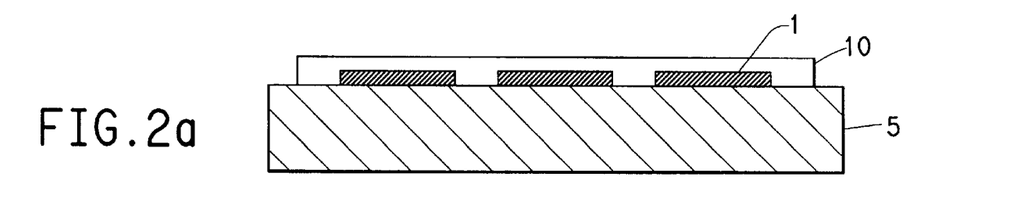
FIG. 2 is a series of views illustrating a sequence of steps in the process of making the bus electrodes and interconnecting electrodes disposed between the bus electrodes and the transparent electrodes on the same glass substrate.
Figure 2B:
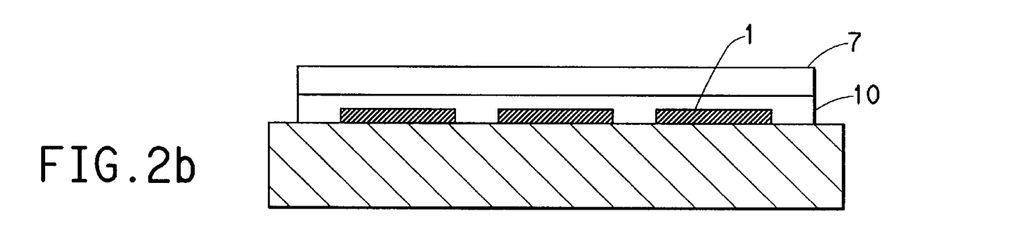
Figure 2C:
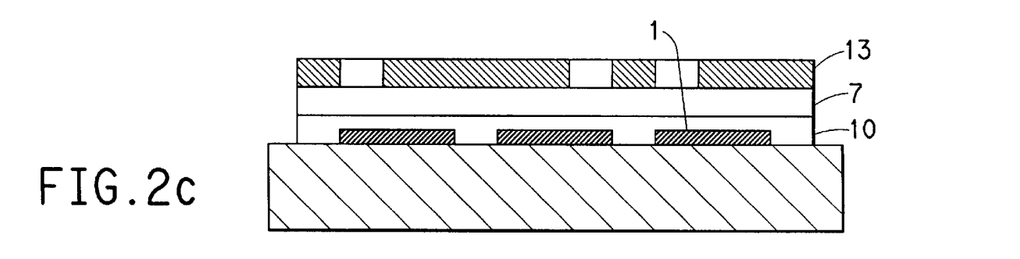
Figure 2D:
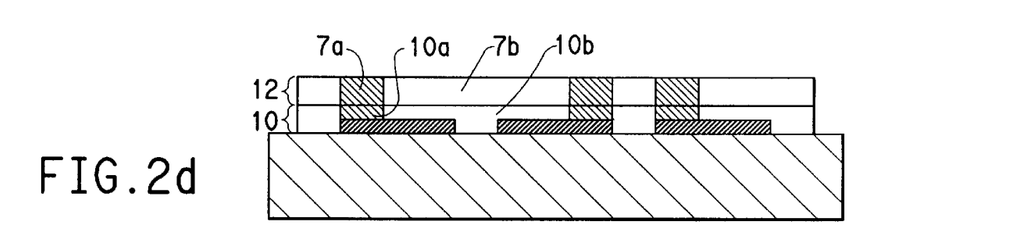
Figure 2E:
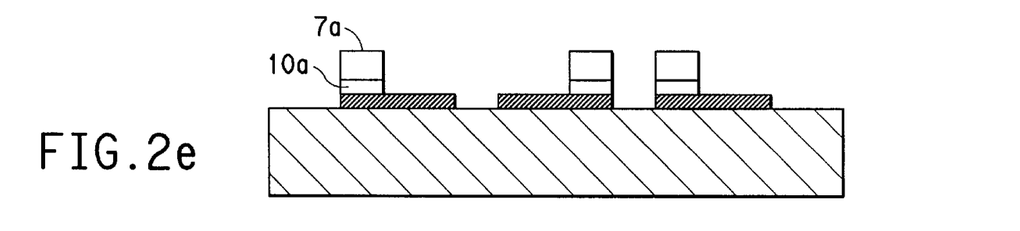

Referencing FIG. 2, the forming process of the first embodiment according to the present invention comprising the following sequential steps:

a. applying over the transparent electrodes 1, which are formed by using $SnO_2$ or ITO in the same manner as in a conventional method as known in the art; a photosensitive thick film composition layer 10 is disposed thereon. The black electrode composition comprises an admixture of (a) conductive particles of at least one of $RuO_2$, ruthenium based polynary oxide or mixtures thereof and may also include additional conductive particles of at least one metal selected from a group of Au, Ag, Pd, Pt and Cu, or combinations thereof, if Cu is present, a non-reducing atmosphere must be used, (b) at least one inorganic binder, (c) organic, carboxylic acid containing polymeric binder, (d) photoinitiation system, and (e) photohardenable monomer (as shown in FIG. 2(a));

b. applying to the first applied black electrode composition layer 10 a photosensitive thick film conductive composition layer 7 for forming the bus electrodes comprising an admixture of (a) conductive particles of at least one metal selected from a group of Au, Ag, Pd, Pt and Cu, or combination thereof, (b) at least one inorganic binder, (c) an organic, carboxylic acid containing polymeric binder, (d) a photoinitiation system, and (e) a photohardenable monomer (as shown in FIG. 2(b)), and a) and b) being followed by a step for drying at between 75° and 100° C. in a nitrogen or air atmosphere oven;

c. imagewise exposing the first black electrode composition layer 10 and the second bus electrode composition layer 7 to actinic radiation (UV source is mainly used) through a phototool or target 13 having a shape corresponding to a pattern of the black and bus electrodes arranged in correlation with the transparent electrodes 1 to define the electrode pattern (as shown in FIG. 2(c)) for the optimum exposure time being determined from an exposure to yield the correct configuration after development;

d. developing the exposed portions 10(a) and 7(a) in the first black electrode composition layer 10 and the second bus electrode composition layer 7 in basic aqueous solution which is 0.8 wt % of sodium carbonate or other aqueous alkaline solutions to remove the unexposed portions 10(b) and 7(b) of the layers 10 and 7 (as shown in FIG. 2(d)) and the developed assemble being optionally dried in an oven under predetermined conditions to volatilize the organic components; and, e. firing the exposed portions 100(a) and 7(a) at temperature of 500°–700° C., depending upon the substrate material, for about two and a half hours to sinter the inorganic binder and conductive components (as shown in FIG. 2(e)).

Figure 3A:
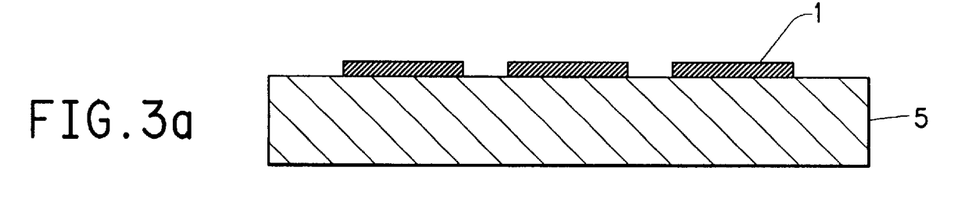
FIG. 3 is a series of views illustrating another sequence of steps in the process of the present invention.
Figure 3B:
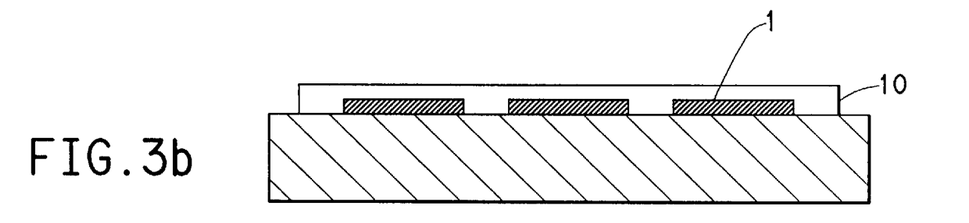
Figure 3C:
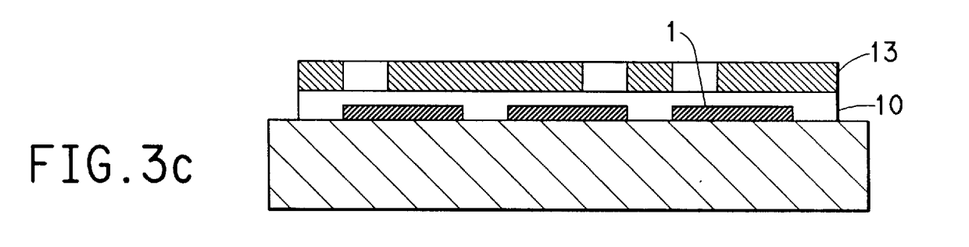
Figure 3D:
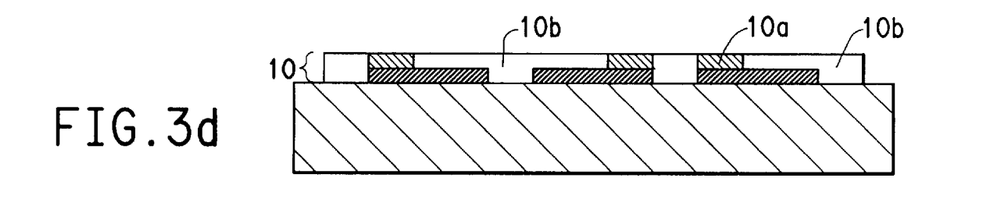
Figure 3E:
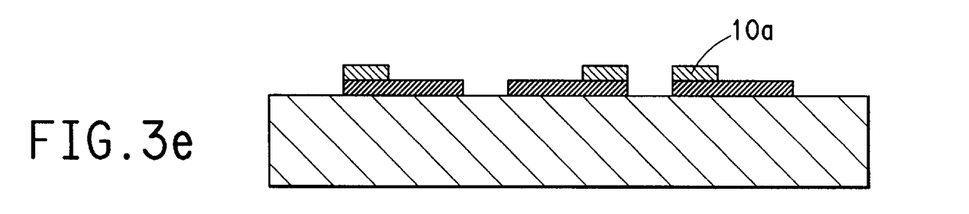
Figure 3F:
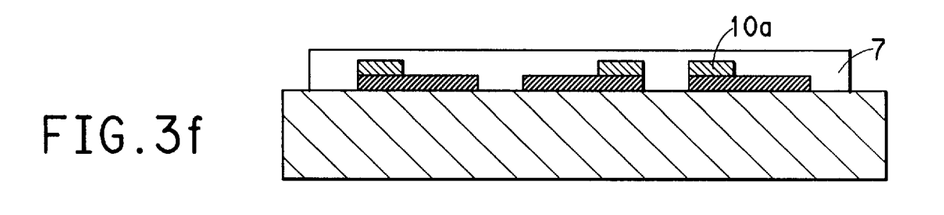
Figure 3G:
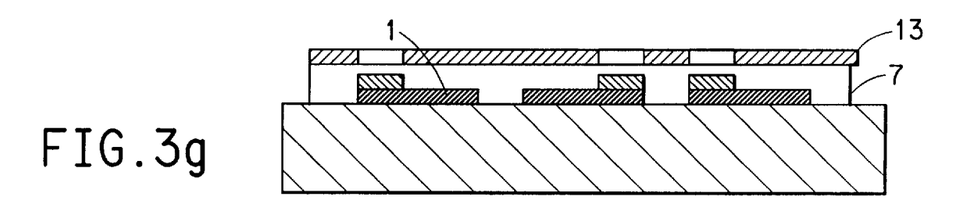
Figure 3I:
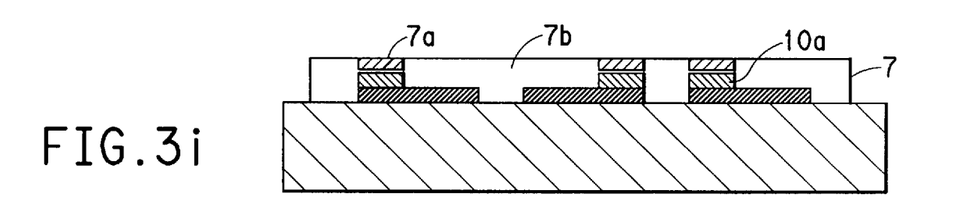

In FIG. 3, the forming process of the second embodiment according to the present invention will be described hereunder. For the convenience of the explanation the same numerals are used for the same components illustrated in FIG. 3 as those in FIG. 2. The method of the second embodiment comprises the sequential steps:

a'. applying over the transparent electrodes 1, which is already formed using $SnO_2$ or ITO in a conventional manner on the glass substrate 5 as a front substrate of the PDP device; a photosensitive thick film composition layer 10 for forming the black electrodes is disposed thereon. The black electrode composition comprises an admixture of (a) conductive particles of at least one of $RuO_2$, ruthenium based polynary oxide or mixtures thereof and may also contain additional conductive particles of at least one metal selected from Au, Ag, Pd, Pt and Cu or combinations thereof. If Cu is present, a non-reducing atmosphere must be used, (b) at least one inorganic binder, (c) organic, carboxylic acid containing polymeric binder, (d) photoinitiation system, and (e) photohardenable monomer, the thick film composition layer 10 being dried at between 75° and 100° C. in a nitrogen or air atmosphere oven (as shown in FIG. 3(*a*) and (*b*));

b'. imagewise exposing the first black electrode composition layer 10 to actinic radiation (UV source is mainly used) through a phototool or target 13 having a shape corresponding to a pattern of the black electrodes arranged in correlation with the transparent electrodes 1 to define the electrode pattern (as shown in FIG. 3(*c*)) for the optimum exposure time being determined from an exposure to yield the correct configuration after development;

c'. developing the exposed portions 10(*a*) of the first black electrode composition layer 10 in basic aqueous solution which is 0.8 wt % of sodium carbonate or other aqueous alkaline solutions to remove the unexposed portions 10(*b*) of the layers 10 (as shown in FIG. 3(*d*)) and the developed assemble being optionally dried in an oven under predetermined conditions to volatilize the organic components;

d'. firing the exposed portions 10(*a*) at temperature of 500°–700° C., depending upon the substrate material, for about two and a half hours to sinter the inorganic binder and conductive components (as shown in FIG. 3(*e*));

e'. applying over the black electrodes 10(*a*) corresponding to the fired and patterned portion 10(*a*) of the first photosensitive thick film composition layer 10, a photosensitive thick film conductive composition layer 7 for forming the bus electrodes comprising an admixture of (a) conductive particles of at least one metal selected from a group of Au, Ag, Pd, Pt and Cu, or combination thereof, (b) at least one inorganic binder, (c) an organic, carboxylic acid containing polymeric binder, (d) a photoinitiation system, and (e) a photohardenable monomer (as shown in FIG. 3(*f*)), and being followed by a step for drying at between 75° and 100° C. in a nitrogen or air atmosphere oven;

f'. imagewise exposing the second bus electrode composition layer 7 to actinic radiation (UV source is mainly used) through a phototarget 13 having a shape corresponding to a pattern of the bus electrodes 7 arranged in correlation with the transparent electrodes 1 and the black electrodes 10(*a*) to define the electrode pattern (as shown in FIG. 3(*g*)) for the optimum exposure time being determined from an exposure to yield the correct configuration after development;

g'. developing the exposed portions 7(*a*) in the second bus electrode composition layer 7 in basic aqueous solution which is 0.8 wt % of sodium carbonate or other aqueous alkaline solutions to remove the unexposed portions 7(*b*) of the layer 7 (as shown in FIG. 3(*h*)) and the developed assemble being optionally dried in an oven under predetermined conditions to volatilize the organic components; and, h'. firing the exposed portions 7(*a*) at temperature of 500°–700° C., depending upon the substrate material, for about two and a half hours to sinter the inorganic binder and conductive components (as shown in FIG. 3(*i*)).

A third embodiment, which is not illustrated, comprises the sequential steps of:

(1) applying a photosensitive black composition on a substrate, wherein the black conductive composition comprises an admixture of (a) conductive particles of at least one of $RuO_2$, ruthenium based polynary oxide or mixtures thereof, (b) at least one inorganic binder, (c) organic, carboxylic acid containing polymeric binder, (d) photoinitiation system, and (e) photohardenable monomer;

(2) applying the photosensitive conductive composition comprised of an admixture of (a) conductive particles of at least one metal selected from a group of Au, Ag, Pd, Pt and Cu, or combinations thereof, (b) at least one inorganic binder, (c) an organic, carboxylic acid containing polymeric binder, (d) a photoinitiation system, and (e) a photohardenable monomer to the substrate;

(3) imagewise exposing the black and conductive compositions to actinic radiation to define the electrode pattern;

(4) developing the exposed black and conductive compositions in basic aqueous solution to remove the compositions in areas not exposed to actinic radiation;

(5) firing the developed conductive compositions.

Referring back to FIG. 1, after the formation of the transparent electrodes 1 associated with the black electrodes 10 and the bus electrodes 7 on the front glass substrate 5 in the manner described above, the front glass assembly is encapsulated in a dielectric 8 and coated with MgO 11. The front glass substrate 5 is then mated with the rear glass substrate 6 where the cell barrier 4 is formed to define a plurality of display cells containing phosphor 3 which was screen-printed therewithin. Also, the electrode formation on the front substrate assembly is perpendicular to the rear glass addressing electrode formation. The space between the front and rear glass substrates 5 and 6 is sealed by sealing glass and at the same time a discharge mixture gas is sealed in the discharge spaces. AC PDP device is thus assembled.

The components of the photoformable black electrode of the present invention will be discussed herein below.

A. Electrically Conductive Particles of Black Electrode Composition

The conductive black compositions of the invention contain $RuO_2$ and/or ruthenium based polynary oxides as a conductive component. The conductive particles may optionally contain precious metals including: gold, silver, platinum, palladium, copper or combinations thereof which are discussed in (B) of this section. Ruthenium based polynary oxides are one type of pyrochlore oxide that is a multicomponent compound of $Ru^{+4}$, $Ir^{+4}$, or their mixture (M") represented by the following general formula $$(M_xBi_{2-x})(M''_yM'_{2-y})O_{7-z}$$

M is chosen from a group consisting of yttrium, thallium, indium, cadmium, lead, copper, and rare earth materials, M' is chosen from a group consisting of platinum, titanium, chromium, rhodium, and antimony, M" is ruthenium, iridium or their mixture, x is 0–2 but x≤1 for univalent copper, y is 0–0.5 but when M' is rhodium or is more than 1 of platinum, titanium, chromium, rhodium, or antimony, y is 0–1, and z is 0–1 but when M is bivalent lead or cadmium, this is at least equal to about x/2.

The ruthenium pyrochlore oxides are found in detail in U.S. Pat. No. 3,583,931.

Preferable ruthenium polynary oxides are bismuth ruthenate $Bi_2Ru_2O_7$, lead ruthenate $Pb_2Ru_2O_6$, $Pb_{1.5}$, $BiO_{0.5}$, $Ru_2O_{6.5}$ and $GdBiRu_2O_6$. These materials can easily be obtained in pure form, they are not adversely affected by glass binders, are stable even when heated to about 1000° C. in air, and are relatively stable even in reducing atmospheres.

The ruthenium oxides and/or ruthenium pyrochlore oxides are used in proportions of 4–50 wt %, preferred 6–30%, more preferred 5–15% and most preferred 9–12%, based on the weight of the entire composition including the organic medium.

B. Electrically Conductive Metal Particles of Black Electrode Composition

The electrically conductive metals may be optionally added to the black composition. Virtually any shape metal powder, including spherical particles and flake (rods, cones, plates) may be used in practicing the invention. The preferred metal powders are gold, silver, palladium, platinum, copper or combinations thereof. It is preferred that the particles be spherical. It has been found that the dispersion of the invention must contain no significant amount of solids having a particle size of less than 0.2 $\mu$m. When particles of this small size are present it is difficult to adequately obtain complete burnout of the organic medium when the films or layers thereof are fired to remove the organic medium and to effect sintering of the inorganic binder and the metal solids. When the dispersions are used to make thick film pastes, which are usually applied by screen printing, the maximum particle size must not exceed the thickness of the screen. It is preferred that at least 80 percent by weight of the conductive solids fall within the 0.5–10 $\mu$m range.

In addition, it is preferred that the surface area/weight ratio of the conductive particles not exceed 20 $m^2$/g, preferably 10 $m^2$/g and more preferably $m^2$/g. When metal particles having a surface area/weight ratio greater than 20 $m^2$/g are used, the sintering characteristics of the accompanying inorganic binder are adversely affected. It is difficult to obtain adequate burnout and blisters may appear.

Often, copper oxide is added to improve adhesion. The copper oxide should be present in the form of finely divided particles, preferably ranging in size from about 0.5 to 5 microns. When present as $Cu_2O$, the copper oxide comprises from about 0.1 to about 3 percent by weight of the total composition, and preferably from about 0.1 to 1.0 percent. Part or all of the $Cu_2O$ may be replaced by molar equivalents of CuO.

C. Inorganic Binders

The inorganic binders, which can also be referred to as glasses or frits, used in this invention help sinter the conductive component particles and can be any composition known in the art provided it has a softening point below the melting point of the conductive components. The softening point of the inorganic binder has considerable influence on the sintering temperature. For the conductive composition of the present invention to be sufficiently sintered on an underlying layer, the glass softening point is about 325°–700° C., preferably about 350°–650° C. and more preferably about 375°–600° C.

If melting takes place below 325° C., organic material will likely be encapsulated and blisters will tend to form in the composition as the organic materials decompose. On the other hand, a softening point above 700° C. will tend to produce a composition with poor adhesion.

The glass frit most preferably used are the borosilicate frits, such as lead borosilicate frit, bismuth, cadmium, barium, calcium or other alkaline earth borosilicate frits. The preparation of such glass frits is well known in the art and consists, for example, of melting together the constituents of the glass in the form of the oxides of the constituents and pouring such molten composition into water to form the frit.

The batch ingredients may, of course, be any compound that will yield the desired oxides under the usual conditions of frit production. For example, boric oxide will be obtained from boric acid, silicon dioxide will be produced from flint, barium oxide will be produced from barium carbonate, etc.

The frit is passed through a fine mesh screen to remove large particles since the solid composition should be agglomerate free. The inorganic binder should have a surface to weight ratio of no more than 10 $m^2$/g. Preferably at least 90 percent by weight of the particles have a particle size of 0.4–10 $\mu$m.

The inorganic binder is preferably 0.01–25 percent by weight of the weight of the conductive or insulating particles. At higher levels of inorganic binder, the bondability to the substrate is reduced.

D. Organic Polymer Binders

Polymer binders are important to the compositions of this invention. They must take into consideration the aqueous-developability and must give a high resolving power. It was found that these requirements were satisfied by selecting the following binders. That is, these binders are copolymers or interpolymers made from (1) nonacidic comonomers comprising $C_{1-10}$ alkyl acrylates, $C_{1-10}$ alkyl methacrylates, styrene, substituted styrenes, or their combinations and (2) acidic comonomers comprising ethylenically unsaturated carboxylic acids containing moiety that are at least 15 wt % of the total polymer weight.

The presence of acidic comonomer components in the composition is important to this technique. The acidic functional group generates the ability to be developed in aqueous bases such as aqueous solutions of 0.8% sodium carbonate. When acidic comonomers are present in concentrations of less than 15%, the composition is not washed off completely with an aqueous base. When the acidic comonomers are present at concentrations greater than 30%, the composition is less stable under development conditions and partial development occurs in the image portions. Appropriate acidic comonomers include ethylenically unsaturated monocarboxylic acids such as acrylic acid, methacrylic acid, or crotonic acid and ethylenically unsaturated dicarboxylic acids such as fumaric acid, itaconic acid, citraconic acid, vinyl succinic acid, and maleic acid, as well as their hemiesters, and in some cases their anhydrides and their mixtures. Because they are cleaner burning in low-oxygen atmospheres, methacrylic polymers are preferred over acrylic polymers.

When the nonacidic comonomers are alkyl acrylates or alkyl methacrylates as mentioned above, it is preferable that these nonacidic comonomers constitute at least 50 wt %, preferably 70–75 wt %, of the polymer binder. When the nonacidic comonomers are styrene or substituted styrenes, it is preferable that these nonacidic comonomers constitute 50 wt % of the polymer binder and that the other 50 wt % is an acid anhydride such as the hemiester of maleic anhydride. A favorable substituted styrene is a-methylstyrene.

Although not preferable, the nonacidic portion of the polymer binder can contain up to about 50 wt % of other nonacidic comonomers as substitutes for the alkyl acrylate, alkyl methacrylate, styrene, or substituted styrene portions of the polymer. Examples include: acrylonitrile, vinyl acetate, acrylamide. However, because it is more difficult for these to completely burn out, it is preferable that less than about 25 wt % of such monomers in the total polymer binder are used. The use of single copolymers or combinations of copolymers as binders are recognized as long as each of these satisfies the various standards above. In addition to the above copolymers, adding small amounts of other polymer binders is possible. For examples of these, polyolefins such as polyethylene, polypropylene, polybutylene, polyisobutylene, and ethylene-propylene copolymers, as well as polyethers that are low alkylene oxide polymers such as polyethylene oxide, can be cited.

The polymers can be produced by those skilled in the art of acrylate polymerization by commonly used solution polymerization techniques.

Typically, such acidic acrylate polymers are produced by mixing α- or β-ethylenically unsaturated acids (acidic comonomers) with one or more copolymerizable vinyl monomer (nonacidic comonomers) in a relatively low-boiling-point (75°–150° C.) organic solvent to obtain a 10–60% monomer mixture solution, then polymerizing the monomers by adding a polymerization catalyst and heating the mixture under normal pressure to the reflux temperature of the solvent. After the polymerization reaction is essentially complete, the acidic polymer solution produced is cooled to room temperature, samples are collected, and the polymer viscosity, molecular weight, and acid equivalents are measured.

Furthermore, it is necessary to keep the molecular weight of the acid-containing polymer binder below 50,000 preferably less than 25,000, and more preferably less than 15,000.

If the above composition is to be coated by screen printing, it is preferable that the Tg (glass transition temperature) of the polymer binder is greater than 90° C.

After screen-printing, said paste is normally dried at temperatures up to 90° C. and those with Tg values less than this temperature generally become very sticky compositions. For substances coated by a means other than screen printing, lower Tg values can be used.

The organic polymer binder is generally present in amounts of 5–45 wt % of the total weight of the dry photopolymerizable layer.

E. Photoinitiators

Suitable photoinitiators are those that are thermally inactive but generate free radicals when exposed to actinic radiation at 185° C. or less. These include substituted or unsubstituted multinucleate quinones that are compounds having 2 intramolecular rings in a conjugated carbon ring system and include, for example, 9,10-anthraquinone, 2-methyl anthraquinone, 2-ethyl anthraquinone, 2-tert-butyl anthraquinone octamethyl antlraquinone, 1,4-naphthoquinone, 9,10-phenanthrene quinone, benz(a)anthracene-7,12-dione, 2,3-naphthacen-5,12, dione, 2-methyl-1,4-naphthoquinone, 1,4-dimethyl anthraquinone, 2,3-dimethyl anthraquinone, 2 phenyl anthraquinone, 2,3-diphenyl anthraquinone, retenequinone, 7,8,9,10 tetrahydronapthacene-5,12-dione, and 1,2,3,4-tetrahydrobenz(a) anthracene-7,12-dione. Other photoinitiators that are useful are described in U.S. Pat. No. 2,760,863, although some are thermally active even at low temperatures such as 85° C. and include adjacent (viscinal) ketaldonyl alcohols, for example, benzoin or pivaloin; acyloin ethers, for example, benzoin methyl and ethyl ethers; hydrocarbon-substituted aromatic acyloins, including α-methyl benzoin, α-allyl benzoin, α-phenyl benzoin, thioxthone and thioxthone derivatives and hydrogen donors.

Photoreducing dyes and reducing agents, those presented in U.S. Pat. Nos. 2,850,445, 2,875,047, 3,097,096, 3,074,974, 3,097,097, and 3,145,104 as well as phenazine, oxazine, and quinone classes Michler's ketone, ethyl Michler's ketone, benzophenone, 2,4,5-triphenyl imidazolyl dimers with hydrogen-donators including leuco dyes and their mixtures (described in U.S. Pat. Nos. 3,427,161, 3,479, 185, and 3,549,367), can be used as initiators. Also, the sensitizers presented in U.S. Pat. No. 4,162,162 are useful with photoinitiators and photoinhibitors. The photoinitiators or photoinitiator system is present in an amount of 0.05 to 10% by weight based on the total weight of the dry photopolymerizable layer.

F. Photohardenable Monomers

The photohardenable monomers component of this invention is comprised of at least one addition polymerizable ethylenically unsaturated compound having at least one polymerizable ethylene group.

Such compounds are capable of forming polymers by being initiated by free radicals and undergoing chain-propagating addition polymerization. The monomer compounds are nongaseous, that is, having boiling points greater than 100° C., and have plasticizing effects on the organic polymer binders.

Preferred monomers that can be used alone or used as combinations with other monomers include t-butyl acrylate and methacrylate, 1,5-pentanediol diacrylate and dimethyacrylate, N,N-dimethylaminoethyl acrylate and methacrylate, ethylene glycol diacrylate and dimethacrylate, 1,4-butanediol diacrylate and dimethacrylate, diethylene glycol diacrylate and dimethacrylate, hexamethylene glycol diacrylate and dimethacrylate, 1,3-propanediol diacrylate and dimethacrylate, decamethylene glycol diacrylate and dimethacrylate, 1,4-cyclohexanediol diacrylate, and dimethacrylate, 2,2-dimethylolpropane diacrylate and dimethacrylate, glycerol diacrylate and dimethacrylate, tripropylene glycol diacrylate and dimethacrylate, glycerol triacrylate and trimethacrylate, trimethylolpropane triacrylate and trimethacrylate, and compounds like those presented in U.S. Pat. No. 3,380,381, 2,2-di(p-hydroxyphenyl) -propane diacrylate, pentaerythritol tetraacrylate and tetramethacrylate, 2,2-di-(phydroxyphenyl)-propane diacrylate, pentaerythritol tetraacrylate and tetramethacrylate, 2,2-di(p-hydroxyphenyl)-propane dimethacrylate, triethylene glycol diacrylate, polyoxyethyl-1,2-di-(p-hydroxyethyl) propane dimethacrylate, bisphenol-A di-(3-methacryloxy-2-hydroxypropyl) ester, bisphenol-A di(3-acryloxy-2-hydroxypropyl) ether, bisphenol-A di(2-methacryloxyethyl) ether, bisphenol-A di(2-acryloxyethyl) ether, 1,4-butanediol di-(3-methacryloxy-2-hydroxypropyl) ether, triethylene glycol dimethacrylate, polyoxypropyl trimethylolpropane triacrylate, butylene glycol diacrylate and dimethacrylate, 1,2,4-butanediol triacrylate and trimethacrylate, 2,2,4-trimethyl-1,3-pentanediol diacrylate and dimethacrylate, 1-phenylethylene-1,2-dimethacrylate, diallyl fumarate, styrene, 1,4-benzenediol dimethacrylate, 1,4-diisopropenyl benzene, and 1,3,5-triisopropenylbenzene.

Ethylenically unsaturated compounds having molecular weights of at least 300, for example, alkylene or polyalkylene glycol diacrylates produced from alkylene glycols or polyalkylene glycols with 1–10 ether bonds of 2-1 5-carbon alkylene glycols and those presented in U.S. Pat. No. 2,927,022, for example, those having several addition-polymerizable ethylene bonds, particularly when they exist as terminal bonds, are also useful.

Other useful monomers are disclosed in U.S. Pat. No. 5,032,490.

Preferred monomers are polyoxyethylated trimethylolpropane triacrylate and methacrylate, ethylated pentaerythritol triacrylate, trimethylolpropane triacrylate and methacrylate, dipentaerythritol monohydroxyphentaacrylate, and 1,10-decanediol dimethacrylate.

Other favorable monomers are monohydroxypolycaprolactone monoacrylate, polyethylene glycol diacrylate (molecular weight of about 200), and polyethylene glycol 400 dimethacrylate (molecular weight of about 400). Unsaturated monomer components are present in amounts of 1–20 wt %, based on the total weight of the dry photopolymerizable layer.

G. Organic Medium

The main purpose of the organic medium is to serve as a vehicle of the dispersion of the finely divided solids of the composition in such form that it can readily be applied to a ceramic or other substrate. Thus, the organic medium must first be one in which the solids are dispersible with an adequate degree of stability. Secondly, the rheological properties of the organic medium must be such that they lend good application properties to the dispersion.

The solvent component of the organic medium, which may be a mixture of solvents, is chosen so as to obtain complete solution therein of the polymer and other organic components. The solvent should be inert (non-reactive) towards the other constituents of the paste composition. The solvent(s) should have sufficiently high volatility to enable the solvent to be evaporated from the dispersion by the application of relatively low levels of heat at atmospheric pressure, however, the solvent should not be so volatile that the paste rapidly dries on a screen, at normal room temperatures, during the printing process. The preferred solvents for use in the paste compositions should have boiling points at atmospheric pressure of less than 300° C. and preferably less than 250° C. Such solvents include aliphatic alcohols, esters of such alcohols, for example, acetates and propionates; terpenes such as pine oil and alpha- or beta-terpineol, or mixtures thereof; ethylene glycol and esters thereof, such as ethylene glycol monobutyl ether and butyl cellosolve acetate; carbitol esters, such as butyl carbitol, butyl carbitol acetate and carbitol acetate and other appropriate solvents such as Texanol (2,2,4-trimethyl-1,3-pentanediol monoisobutyrate).

H. Additional Components

Additional components known in the art may be present in the composition including dispersants, stabilizers, plasticizers, release agents, dispersing agents, stripping agents, antifoaming agents, and wetting agents. A general disclosure of suitable materials is presented in U.S. Pat. No. 5,032,490.

Bus Conductor Compositions

The bus conductor compositions of the present invention are commercially available thick film photosensitive conductor compositions. The preferred compositions for use in this invention contain silver particles, UV polymerizable vehicle and glass frits.

The conducting phase is the major component of the composition and consists of silver particles ranging in size from 0.05–20 micronmeters (micron) and may be random or flake in shape and preferably the silver particle size range is 0.3–10 micron in the composition associated with UV polymerizable vehicles. The preferred composition contains 66% silver particles by weight of the fully formulated thick film paste; wherein the particles have a surface area of 0.34 $m^2/g$.

The silver conductor composition for forming bus electrodes contains 1–10% by weight of finely divided inorganic particulate non-glass forming materials which are refractory or their precursors which include: aluminum oxide, copper oxide, cadmium oxide, gadolinium oxide, zirconium oxide, cobalt/iron/chromium oxide, aluminum and copper. These oxides or oxide precursors have a particle size range of 0.05–44 micron, with at least 80% by weight of the particles in the 0.1–5 micron range. The composition also contains 5–20% by weight of glass frit having a softening point range of 325°–600° C. Preferred glass frits include the lead borosilicate-type glasses; an especially preferred composition is (mole %): PbO (53.1), $B_2O_3$ (2.9), $SiO_2$ (29.0), $TiO_2$ (3.0), $ZrO_2$ (3.0), ZnO (2.0), $Na_2O$ (3.0), and CdO (4.0). These formulations of the glass frit and appropriate additives are to achieve the requirement of the fine line fired metallization not reacting or dissolving, nor breaking or losing adhesion to the underlying black electrodes during the one-hour immersion in molten overglaze at 600° C.

The silver conductor composition may further contain 10–30% by weight of a photosensitive vehicle in which the above mentioned particulate materials are dispersed. An example of such photosensitive vehicle is a solution of polymethyl methacrylate and a polyfunctional monomer. The monomer should have low volatility in order to minimize its evaporation during the preparation of the silver conductor composition paste and the printing/drying steps prior to UV curing. The photosensitive vehicle also contains solvents and UV sensitive initiators. A preferred UV polymerizable vehicle contains a polymer based on methyl methacrylate/ethyl acrylate// 95/5 (by weight) and the silver conductor composition is formulated so that it is a free-flowable paste with a viscosity between 50 and 200 Pascal seconds.

Suitable solvents for the vehicles include, but are not limited to butyl carbitol acetate and beta-terpineol. Additionally, the vehicle can also contain dispersing agents, stabilizers, etc.

The resulting silver conductor electrodes may be coated with an overglaze composition containing 85 parts of a glass frit (composition, mole %: PbO, 68.2; $SiO_2$, 12.0; $B_2O_3$, 14.1; CdO, 5.7; softening point of 480° C.) and 14 parts of an ethyl cellulose vehicle. The overglazed electrode composite so obtained is useful in preparing AC PDP.

Transparent Compositions

The transparent electrodes are formed using $SnO_2$ or ITO by ion spattering or plating, chemical vapor deposition or electric deposition techniques. Such transparent electrode configurations and the formation processes are well known in the art of the conventional AC PDP technology.

Preparation of Photoactive Aqueous Processable Paste

A. Preparation of Organic Vehicle

The solvent and acrylic polymer were mixed and heated with stirring to 100° C. Heating and stirring was continued until all the binder polymer had dissolved. The solution was then cooled to 80° C. and the remaining organic components added. This mixture was then stirred at 80° C. until all the solids had dissolved. The solution was passed through a 325 mesh filter screen and allowed to cool.

B. Preparation of Glass Frit

The glass frit was used as available, or if necessary was prepared by water milling in a Sweco Mill using 0.5 in. diameter by 0.5 in. long alumina cylinders. The glass frit mixture was then either freeze dried or hot air dried. Hot air drying was normally done at a temperature of 150° C.

C. Paste Formulation

The pastes was prepared under yellow light by mixing the organic vehicle, monomer or monomers, and other organic components in a mixing vessel. The inorganic materials were then added to the mixture of organic components. The total composition was then mixed until the inorganic powders were wetted by the organic materials. The mixture was then either roll milled using a three roll mill or mulled on a Hoover Automatic Muller, Model M5. The pastes were then either used directly, or screened through a 635 mesh screen. The paste viscosity at this point could be adjusted with the appropriate vehicle or solvent to achieve a viscosity optimum for processing.

D. Process Conditions

Care was taken to avoid dirt contamination in the process of preparing paste compositions and in preparing parts, since such contamination can lead to defects. The paste was applied to glass substrates by screen printing using 200–400 mesh screens, depending upon the paste composition and the desired dried thickness. The parts were dried at ~80° C. in a nitrogen or air atmosphere oven. The dried coating thickness was measured at 5–14 microns for a single layer of material.

In many cases, the parts were tested both as a single layer, described above, and/or as a two layer structure. In the case of the two layer structure, the Example paste was first deposited on the glass substrate by screen printing using 200–400 mesh screens, depending upon the paste composition and the desired dried thickness. The parts were then dried at ~80° C. in a nitrogen or air atmosphere oven. Next, the parts were overprinted with DuPont Fodel® DC202 photoimageable Ag conductor paste by screen printing using 325–400 mesh screens. The parts were again dried at ~80° C. The dried coating thickness for the two layer structure was measured at 15–19 microns.

The parts, either single layer or two layer structure, were then exposed through a phototool with a collimated UV exposure source. The exposed parts were developed using a conveyorized spray processor containing 0.4–0.85% by weight sodium carbonate in water as the developer solution. The developer temperature was maintained at ~30° C., and the developer solution was sprayed at 10–20 psi. The optimum exposure time and development rate was determined by preparing a matrix of parts with a range of exposure times and development rates for each composition. Microscopic examination of the parts after development yielded information on the best exposure time and development rate to reproducibly obtain the minimum line width or via diameter for each composition. The developed parts were dried by blowing off the excess water, after development, with a forced air stream. The dried parts were then normally fired in an air atmosphere at peak temperatures of 540° C. to 605° C. and profiles specific to the intended applications.

The resolution was determined from parts that reproducibly yielded the finest line spacing for which the lines were straight and non-overlapping. The photospeed was determined by measuring the light intensity at the surface of the dried photosensitive conductor composition with a light meter and multiplying by the time required for optimum exposure.

EXAMPLES

All results labeled NA were not collected at the time the samples were made. All compositional components for compositions of all Examples are given in parts.

Examples 1–6

Parts were prepared as described above, using compositions given below. They were tested as a two layer structure with Fodel® DC202 photoimageable Ag conductor.

The parts showed white or slightly gray color of DC202 top conductor layer and black on substrate side color in appearance after cofiring the two layer structure and provide very good contrast for AC PDP device. Additional experimental results for Example 1–6 are shown below the composition table.

| Example | 1 | 2 | 3 | 4 | 5 | 6 |
|---|---|---|---|---|---|---|
| Ruthenium Oxide I | 20.0 | | | 6.0 | | |
| Polynary Oxide I | | 20.0 | | | | |
| Polynary Oxide II | | | 20.0 | 8.6 | 16.7 | 25.0 |
| Glass Frit I | 40.0 | 40.0 | 40.0 | | 33.3 | 25.0 |
| Glass Frit II | | | | 15.0 | | |
| Glass Frit III | | | | 30.1 | | |
| Niobium Pentoxide | | | | 0.3 | | |
| Vehicle I | 40.0 | 40.0 | 40.0 | 40.0 | 50.0 | 50.0 |
| Examples 1–6 Results | | | | | | |
| Top layer Ag Color | Gray | White | White | White | White | White |
| Substrate Side Color | Black | Black | Black | Black | Black | Black |
| Dried Thickness (um) | 18.0 | 18.5 | 19.0 | 19.5 | 14.0 | 14.0 |
| Exposure Energy (mJ/cm$^2$) | 1500 | 1500 | 1500 | 1500 | 1000 | 1000 |
| Resolution (um) | <50 | <50 | <50 | <50 | <30 | <30 |

Examples 7–12

Parts were prepared as described above, using the compositions given below. Examples 7–12 were tested as a single layer of material only. They were not tested with a top layer of Fodel® DC202 photoimageable Ag conductor.

The parts showed various colors, depending upon the amount of Ruthenium Oxide II present in the sample. Examples 7 and 8 were considered too light in color to provide sufficient contrast for display panels. Examples 9 and 10 were medium gray in color and would provide marginal contrast for display panels. Examples 11 and 12 were charcoal gray in color and would provide adequate contrast for display panels. Examples 11 and 12 did not sinter fully at 600° C. peak firing temperatures, reducing adhesion to the substrate. Additional experimental results for Examples 7–12 are shown below the composition table.

| Example | 7 | 8 | 9 | 10 | 11 | 12 |
|---|---|---|---|---|---|---|
| Ag | 63.00 | 64.48 | 64.64 | 60.60 | 61.44 | 53.32 |
| Ruthenium Oxide II | 0.60 | 1.24 | 3.20 | 3.00 | 6.40 | 12.40 |
| Glass Frit IV | | | | 2.70 | 1.44 | 1.40 |
| Glass Frit I | 1.35 | 1.40 | 1.44 | | | |
| Monomer II | 1.05 | 1.09 | 1.12 | | | |
| Monomer I | 4.20 | 4.34 | 4.48 | | | |
| Monomer III | | | | 2.25 | 2.40 | 2.33 |
| Vehicle II | | | | 29.10 | 31.04 | 30.07 |
| Vehicle I | 24.00 | 24.80 | 25.60 | | | |
| CBT | 0.15 | 0.16 | 0.16 | 0.09 | 0.10 | 0.09 |
| Malonic Acid | | | | 0.06 | 0.06 | 0.06 |
| Texanol | 4.50 | 4.65 | 4.80 | 2.25 | 2.40 | 2.33 |
| Examples 7–12, Results | | | | | | |
| Color | light gray | gray | medium gray | medium gray | charcoal gray | charcoal gray |
| Dried Thickness ($\mu$m) | 9.7 | 10.1 | 9.7 | 12.7 | 12.5 | 12.9 |
| Fired Thickness ($\mu$m) | 6.3 | 6.8 | 8.0 | 7.0 | 8.5 | 9.3 |

-continued

| Example | 7 | 8 | 9 | 10 | 11 | 12 |
|---|---|---|---|---|---|---|
| Exposure Energy (mJ/cm$^2$) | 1050 | 1350 | 2250 | 1800 | 675 | 675 |
| Resolution ($\mu$m) | ≦25 | ≦25 | ≦25 | ≦25 | ≦25 | ≦25 |

Examples 13–16

Parts were prepared as described above, using the compositions given below with the concentration in parts. Examples 13 and 14 were tested as a single layer of material only. They were not tested with a top layer of Fodel® DC202 photoimageable Ag conductor. Examples 15 and 16 were tested as single layer parts and as a two layer structure with Fodel® DC202 photoimageable Ag conductor.

The parts showed various colors, depending upon the amount of Ruthenium Oxide II present in the sample. Examples 13 and 14 were medium gray in color and would provide marginal contrast for display panels. Examples 15 and 16 were black in color and would provide very good contrast for display panels. Examples 14, 15 and 16 demonstrated marginal sintering at 600° C. peak firing temperatures, reducing adhesion to the substrate. The DC202 Ag conductor layer, top layer in the two layer structure, was gray in appearance after cofiring the two layer structure parts of Examples 15 and 16. Normally, the DC202 conductor fired on glass substrates at 600° C. is white in color. Additional experimental results for Examples 13–16 are shown below the composition table.

| Example | 13 | 14 | 15 | 16 |
|---|---|---|---|---|
| Ag | 62.62 | 62.62 | 37.20 | 31.62 |
| Ruthenium Oxide II | 3.10 | 3.10 | 22.32 | 18.91 |
| Glass Frit IV | | | 6.20 | 10.23 |
| Glass Frit V | 2.79 | | | |
| Glass Frit VII | | 1.40 | | |
| Glass Frit VI | | 1.40 | | |
| Monomer III | 2.33 | 2.33 | 2.33 | 2.33 |
| Vehicle II | 30.07 | 30.07 | 30.07 | 30.07 |
| CBT | 0.09 | 0.09 | 0.09 | 0.09 |
| Malonic Acid | 0.06 | 0.06 | 0.06 | 0.06 |
| Texanol | 2.33 | 2.33 | 2.33 | 2.33 |
| Examples 26–30, Single Layer Results | | | | |
| Color | medium gray | medium gray | black | black |
| Dried Thickness ($\mu$m) | 12.1 | 12.5 | 6.5 | 6.7 |
| Fired Thickness ($\mu$m) | 6.4 | 7.7 | NA | NA |
| Exposure Energy (mJ/cm$^2$) | 450 | 450 | 2250 | 3600 |
| Resolution ($\mu$m) | ≦25 | ≦25 | ≦25 | ≦25 |
| Examples 15 and 16, Two Layer Structure Results | | | | |
| Top Layer Ag Color | | | gray | gray |
| Substrate Side Color | | | black | black |
| Dried Thickness ($\mu$m) | | | 17.6 | 17.2 |
| Fired Thickness ($\mu$m) | | | 10.6 | 15.8 |
| Exposure Energy (mJ/cm$^2$) | | | 450 | 450 |
| Resolution ($\mu$m) | | | ≦25 | ≦25 |

Examples 17–22

Parts were prepared as described above, using the compositions given below with the concentration in parts. Examples 17 and 18 were tested as a single layer of material only. They were not tested with a top layer of Fodel® DC202 photoimageable Ag conductor. Examples 19–22 were tested as single layer parts and as a two layer structure with Fodel® DC202 photoimageable Ag conductor.

The parts showed various colors, Examples 19–22 were black in color and would provide very good contrast for display panels. The DC202 Ag conductor layer, top layer in the two layer structure, was white in appearance after cofiring the two layer structure parts of Examples 19–22. Additional experimental results for Examples 17–22 are shown below the composition table.

| Example | 17 | 18 | 19 | 20 | 21 | 22 |
|---|---|---|---|---|---|---|
| Ag | 62.66 | 54.83 | 36.15 | 30.73 | 24.70 | 24.70 |
| Pyrochlore III | 1.21 | 9.04 | 21.69 | 18.38 | 15.06 | 15.06 |
| Glass Frit IV | | | 1.36 | 6.03 | 9.94 | 11.15 | 15.06 |
| Glass Frit I | 1.36 | | | | | |
| Monomer II | 1.05 | | | | | |
| Monomer I | 4.22 | | | | | |
| Monomer III | | 2.26 | 2.26 | 2.26 | 2.26 | 2.26 |
| Vehicle II | | 29.22 | 29.22 | 29.22 | 29.22 | 29.19 |
| Vehicle I | 24.10 | | | | | |
| CBT | 0.15 | 0.09 | 0.09 | 0.09 | 0.09 | 0.09 |
| Malonic Acid | | 0.06 | 0.06 | 0.06 | 0.06 | 0.06 |
| Texanol | 4.52 | 2.26 | 2.26 | 2.26 | 2.26 | 2.26 |
| Examples 17–22, Single Layer Results | | | | | | |
| Color | gray | charcoal gray | black | black | black | black |
| Dried Thickness ($\mu$m) | 10.2 | 11.6 | 6.8 | 7.3 | 6.6 | 7.6 |
| Fired Thickness ($\mu$m) | 6.4 | 7.4 | NA | NA | NA | 2.6 |
| Exposure Energy (mJ/cm$^2$) | 1350 | 1125 | 1200 | 975 | 1200 | 900 |
| Resolution ($\mu$m) | ≦25 | ≦25 | ≦25 | ≦25 | ≦25 | ≦25 |
| Examples 19–22, Two Layer Structure Results | | | | | | |
| Top Layer Ag Color | | | white | white | white | white |
| Substrate Side Color | | | black | black | black | black |
| Dried Thickness ($\mu$m) | | | 17.4 | 16.0 | 16.6 | NA |
| Fired Thickness ($\mu$m) | | | 8.6 | 7.7 | 6.9 | 6.6 |
| Exposure Energy (mJ/cm$^2$) | | | 450 | 450 | 450 | 450 |
| Resolution ($\mu$m) | | | ≦40 | ≦35 | ≦25 | ≦40 |

Examples 23–25

Parts were prepared as described above, using the compositions given below. Examples 23–25 were tested as a single layer of material only. They were not tested with a top layer of Fodel® DC202 photoimageable Ag conductor.

The parts showed various fired colors, depending upon the amount of pigment present in the sample. Examples 24 and 25 were considered too light in color to provide sufficient contrast for display panels. Example 23 was medium gray in color and would provide marginal contrast for display panels. All samples showed a greenish color on the substrate side. This color might cause a perceptible shift in the display image color, an undesirable effect. Examples 24 and 25 did not sinter fully at 600° C. peak firing temperatures, reducing adhesion to the substrate. Additional experimental results for Examples 23–25 are shown below the composition table.

| Example | 23 | 24 | 25 |
|---|---|---|---|
| Ag | 58.85 | 61.91 | 61.91 |
| Pigment | 6.13 | 3.07 | 3.07 |
| Glass Frit IV | 1.38 | | |
| Glass Frit V | | | 2.76 |
| Glass Frit VIII | | 1.38 | |
| Glass Frit VI | | 1.38 | |

-continued

| Example | 23 | 24 | 25 |
|---|---|---|---|
| Monomer III | 2.30 | 2.30 | 2.30 |
| Vehicle II | 29.73 | 29.73 | 29.73 |
| CBT | 0.09 | 0.09 | 0.09 |
| Malonic Acid | 0.06 | 0.06 | 0.06 |
| Texanol | 2.30 | 2.30 | 2.30 |
| Examples 23–25, Results | | | |
| Color | medium gray | light gray | light gray |
| Dried Thickness ($\mu$m) | 13.3 | 12.3 | 12.1 |
| Fired Thickness ($\mu$m) | 7.1 | 5.5 | 4.9 |
| Exposure Energy (mJ/cm$^2$) | 675 | 450 | 450 |
| Resolution ($\mu$m) | $\leq$25 | $\leq$25 | $\leq$25 |

Examples 26–30

Parts were prepared as described above, using the compositions given below. Examples 26–30 were tested as single layer parts and as a two layer structure with Fodel® DC202 photoimageable Ag conductor.

The parts showed various colors, Examples 26 and 30 were very dark gray in color and would provide good contrast for display panels. Examples 27–29 were black in color and would provide very good contrast for display panels. The DC202 Ag conductor layer, top layer in the two layer structure, was gray in appearance after cofiring the two layer structure parts of Examples 26, 28 and 29. The DC202 Ag conductor layer, top layer in the two layer structure, was white in appearance after cofiring the two layer structure parts of Examples 27 and 30. Additional experimental results for Examples 13–16 are shown below the composition table.

| Example | 26 | 27 | 28 | 29 | 30 |
|---|---|---|---|---|---|
| Ag | 24.31 | 24.31 | 24.31 | 24.31 | 24.31 |
| Polynary Oxide IV | 14.83 | | | | |
| Polynary Oxide V | | 14.83 | | | |
| Polynary Oxide VI | | | 14.83 | | |
| Polynary Oxide VI | | | | 14.83 | |
| Polynary Oxide I | | | | | 14.83 |
| Glass Frit IV | 10.97 | 10.97 | 10.97 | 10.97 | 10.97 |
| Monomer III | 2.22 | 2.22 | 2.22 | 2.22 | 2.22 |
| Vehicle II | 28.73 | 28.73 | 28.73 | 28.73 | 28.73 |
| CBT | 0.09 | 0.09 | 0.09 | 0.09 | 0.09 |
| Malonic Acid | 0.06 | 0.06 | 0.06 | 0.06 | 0.06 |
| Texanol | 2.22 | 2.22 | 2.22 | 2.22 | 2.22 |
| Example 26–30, Single Layer Results | | | | | |
| Color | very dark gray | black | black | black | very dark gray |
| Dried Thickness ($\mu$m) | 7.6 | 7.5 | 5.5 | 7.1 | 7.3 |
| Fired Thickness ($\mu$m) | 4.1 | 3.3 | 2.6 | 3.4 | 3.2 |
| Exposure Energy (mJ/cm$^2$) | 900 | 900 | 1200 | 900 | 900 |
| Resolution ($\mu$m) | $\leq$25 | $\leq$25 | $\leq$25 | $\leq$25 | $\leq$25 |
| Examples 26–30, Two Layer Structure Results | | | | | |
| Top Layer Ag Color | gray | white | gray | gray | white |
| Substrate Side Color | very dark gray | black | black | black | very dark gray |
| Dried Thickness ($\mu$m) | NA | NA | NA | NA | NA |
| Fired Thickness ($\mu$m) | 9.3 | 7.7 | 8.5 | 9.7 | 7.5 |
| Exposure Energy (mJ/cm$^2$) | 450 | 450 | 450 | 450 | 450 |
| Resolution ($\mu$m) | $\leq$30 | $\leq$25 | $\leq$25 | $\leq$25 | $\leq$25 |

GLOSSARY

A. Inorganics

Glass Frit I: (component weight %) $Bi_2O_3$ (82.0), PbO (11.0), $B_2O_3$ (3.5), $SiO_2$ (3.5), surface area 1.5–2.5 m$^2$/gm, softening point 370° C.

Glass Frit II: (component weight %) PbO (66.0), $Al_2O_3$ (0.8), ZnO (6.6), $B_2O_3$ (11.8), $SiO_2$ (14.8), surface area 3.1–4.1 m$^2$/gm, softening point 453° C.

Glass Frit III: (component weight %) PbO (62.1), $Al_2O_3$ (2.6), ZnO (2.7), $B_2O_3$ (1.8), $SiO_2$ (30.8), surface area 4.3–5.5 m$^2$/gm, softening point 500° C.

Glass Frit IV: (component weight %) $Bi_2O_3$ (82.0), PbO (11.0), $B_2O_3$ (3.5), $SiO_2$ (3.5), $d_{50}$=0.45–0.60 $\mu$m.

Glass Frit V: (component weight %) PbO (80.5), $SiO_2$ (6.0), $B_2O_3$ (12.0), ZnO (1.5), surface area 1.5–3.0 m$^2$/gm.

Glass Frit VI: (component weight %) $SiO_2$ (13.8), $Al_2O_3$ (4.9), $B_2O_3$ (28.1), CaO (1.1), ZnO (17.2), $Bi_2O_3$ (34.9), surface area~1.8 m$^2$/gm.

Glass Frit VII: (component weight %) $Al_2O_3$ (13.0), $B_2O_3$ (1.0), ZnO (16.0), CuO (5.1), $P_2O_5$ (61.0), $Ag_2O$ (3.9).

Glass Frit VIII: (component weight %) CuO (30.0), $B_2O_3$ (50.0), $Ag_2O$ (20.0).

Silver: Spherical silver powder; particle size, $d_{50}$=1.9–2.6 $\mu$m.

Ruthenium Oxide I: $RuO_2$, surface area 11.4–15.1 m$^2$/gm.

Ruthenium Oxide II: $RuO_2$, surface area 27.5–32.5 m$^2$/gm.

Polynary Oxide I: $GdBiRu_2O_7$, surface area 2.7–3.3 m$^2$/gm.

Polynary Oxide II: $Pb_2Ru_2O_6$, surface area 7.2–8.9 m$^2$/gm.

Polynary Oxide III: $Pb_2Ru_2O_6$, surface area 8.5–11.3 m$^2$/gm.

Polynary Oxide IV: $Co_2Ru_2O_6$,

Polynary Oxide V: $PbBiRu_2O_{6.5}$,

Polynary Oxide VI: $Cu_xBi_{2-x}Ru_2O_7$ where x=0–1,

Polynary Oxide VII: $Bi_2Ru_2O_7$, surface area 9.5–12.5 m$^2$/gm.

Pigment: Copper Chromite,

Niobium Pentoxide: $Nb_2O_5$, surface area 5.8–7.0 m$^2$/gm.

B. Polymeric Binders

Polymer I: Copolymer of 75% methylmethacrylate and 25% methacrylic acid, Mw~=7000, Tg=120° C., Acid No.=I64.

Polymer II: Sarbox® SB 510 E35, aromatic acid methacrylate half ester, available from Sartomer Company Inc., Exton, Pa.

Polymer III: PVP/VA S-630, copolymer of 60% vinylpyrrolidone and 40% vinyl acetate. K-value=30–50.

C. Monomers

Monomer I: TEOTA 1000—Polyethoxylated trimethylolpropane triacrylate. Mw~1162.

Monomer II: TMPTA—Trimethylolpropane triacrylate.

Monomer III: TMPEOTA—Trimethylolpropane ethoxy triacrylate. Mw~428.

D. Solvents beta-Terpineol: 1-methyl-1-(4-methyl-4-hydroxycyclohexyl)ethene.

Carbitol acetate: Di(ethylene glycol) ethyl ether acetate

Texanol: 2,2,4-trimethyl-1,3-pentanediol monoisobutyrate

E. Photoinitiators

Irgacure 651: 2,2-Dimethoxy-1,2-diphenylethan-1-one

ITX: Isopropyl thioxanthone

EPD: Ethyl 4-(dimethylamino) benzoate

F. Stabilizer

TAOBN: 1,4,4-Trimethyl-2,3-diazabicyclo [3.2.2]-non-2-ene-N,N'-dioxide.

G. Additives

BT: 1,2,3-Benzotriazole.

CBT: 1 H-Benzotriazole Carboxylic Acid

Malonic Acid

| H. Vehicles | Vehicle Number | |
| --- | --- | --- |
| Componeut | I | II |
| Texanol | 52.11 | 98.1 |
| Polymer I | 38.82 | 54.9 |
| Polymer II |  | 53.4 |
| Irgacure 651 | 2.74 | 5.9 |
| ITX | 2.31 | 17.8 |
| EPD | 2.31 | 17.8 |
| Polymer III | 1.64 | 3.1 |
| TAOBN | 0.07 | 0.13 |

I. Miscellaneous

DuPont Fodel® DC202—photoimageable Ag conductor paste available from E. I. du Pont de Nemours and Company, Wilmington, Del.

What is claimed is:

1. A method of fabricating an AC plasma display panel device comprising front and rear insulating substrates spaced apart from each other, and an electrode arrangement composed of groups of electrode composites respectively formed on the front and rear insulating substrates with specified electrode patterns, which are positioned face to face in an orthogonal relationship across a discharge space filled with ionizable gas between the insulating substrates, characterized in that the method of forming the electrode composites on at least the front insulating substrate comprising the sequential steps of:
   (1) applying a photosensitive black composition on at least the front insulating substrate, wherein the photosensitive black composition comprises an admixture of (a) conductive particles of at least one of $RuO_2$, ruthenium based polynary oxide or mixtures thereof, (b) at least one inorganic binder, (c) organic, carboxylic acid containing polymeric binder, (d) photoinitiation system, and (e) photohardenable monomer;
   (2) imagewise exposing the photosensitive black composition to actinic radiation to define the specified pattern;
   (3) developing the exposed black composition in basic aqueous solution to remove the composition in areas not exposed to actinic radiation;
   (4) firing the developed black composition, forming a black conductive component on the substrate;
   (5) applying a photosensitive conductive composition which forms a conductor electrode and comprises an admixture of (a) conductive particles of at least one metal selected from a group of Au, Ag, Pd, Pt and Cu, or combinations thereof, (b) at least one inorganic binder, (c) organic, carboxylic acid containing polymeric binder, (d) photoinitiation system, and (e) photohardenable monomer;
   (6) imagewise exposing the photosensitive conductive composition to actinic radiation to define the electrode pattern;
   (7) developing the exposed conductive composition in basic aqueous solution to remove the composition in areas not exposed to actinic radiation;
   (8) firing the developed conductive composition forming the conductor electrodes on top of the arrangement of black electrodes on the substrate.

2. The method of claim 1 wherein the photosensitive black composition further comprises an admixture of (f) conductive particles of at least one metal selected from a group of Au, Ag, Pd, Pt and Cu, or combinations thereof.

3. A method of fabricating an AC plasma display panel device comprising front and rear insulating substrates spaced apart from each other, and an electrode arrangement composed of groups of electrode composites respectively formed on the front and rear insulating substrates with specified electrode patterns, which are positioned face to face in an orthogonal relationship across a discharge space filled with ionizable gas between the insulating substrates, characterized in that the method of forming the electrode composites on at least the front insulating substrate comprising the sequential steps of:
   (1) applying a photosensitive black composition on at least the front insulating substrate, wherein the photosensitive black composition comprises an admixture of (a) conductive particles of at least one of $RuO_2$, ruthenium based polynary oxide or mixtures thereof, (b) at least one inorganic binder, (c) organic, carboxylic acid containing polymeric binder, (d) photoinitiation system, and (e) photohardenable monomer;
   (2) imagewise exposing the photosensitive black composition to actinic radiation to define the specified pattern;
   (3) applying a photosensitive conductive composition comprised of an admixture of (a) conductive particles of at least one metal selected from a group of Au, Ag, Pd, Pt and Cu, or combinations thereof, (b) at least one inorganic binder, (c) an organic, carboxylic acid containing polymeric binder, (d) a photoinitiation system, and (e) a photohardenable monomer to the substrate;
   (4) imagewise exposing the photosensitive conductive composition to actinic radiation to define the electrode pattern;
   (5) developing the exposed conductive compositions in basic aqueous solution to remove the exposed black composition and exposed conductive composition in areas not exposed to actinic radiation;
   (6) firing the developed black composition and conductive composition.

4. The method of claim 3 wherein the photosensitive black composition further comprises an admixture of (f) conductive particles of at least one metal selected from a group of Au, Ag, Pd, Pt and Cu, or combinations thereof.

5. A method of fabricating an AC plasma display panel device comprising front and rear insulating substrates spaced apart from each other, and an electrode arrangement composed of groups of electrode composites respectively formed on the front and rear insulating substrates with specified electrode patterns, which are positioned face to face in an orthogonal relationship across a discharge space filled with ionizable gas between the insulating substrates, characterized in that the method of forming the electrode composites on at least the front insulating substrate comprising the sequential steps of:
   (1) applying a photosensitive black composition on at least the front insulating substrate, wherein the photosensitive black composition comprises an admixture of (a) conductive particles of at least one of $RuO_2$, ruthenium based polynary oxide or mixtures thereof, (b) at least one inorganic binder, (c) organic, carboxylic acid containing polymeric binder, (d) photoinitiation system, and (e) photohardenable monomer;
   (2) applying a photosensitive conductive composition comprised of an admixture of (a) conductive particles of at least one metal selected from a group of Au, Ag, Pd, Pt and Cu, or combinations thereof, (b) at least one inorganic binder, (c) an organic, carboxylic acid containing polymeric binder, (d) a photoinitiation system, and (e) a photohardenable monomer to the substrate;

(3) imagewise exposing the photosensitive black composition and the photosensitive conductive composition to actinic radiation to define the electrode pattern;

(4) developing the exposed black composition and the exposed conductive composition in basic aqueous solution to remove the exposed black composition and the exposed conductive composition in areas not exposed to actinic radiation;

(5) firing the developed black composition and conductive composition.

6. The method of claim 5 wherein the photosensitive black composition further comprises an admixture of (f) conductive particles of at least one metal selected from a group of Au, Ag, Pd, Pt and Cu, or combinations thereof.

7. The method as in one of claims 1–6, wherein the photosensitive black composition is applied in the form of a paste followed by a drying step.

8. The method as in one of claims 1–6, wherein the photosensitive black composition is applied in the form of a dry film.

9. The method as in one of claims 1–6, wherein the photosensitive conductive composition is applied in the form of a paste followed by a drying step.

10. The method as in one of claims 1–6, wherein the photosensitive conductive composition is applied in the form of a dry film.

11. The method as in one of claims 1–6, wherein the photosensitive black composition is applied on a transparent electrode arrangement with an underlying substrate.

12. The method as in one of claims 1–6, wherein the photosensitive black composition is applied on a transparent dielectric arrangement with an underlying substrate.

\* \* \* \* \*